United States Patent [19]  [11] Patent Number: 5,075,439
Busch et al.  [45] Date of Patent: Dec. 24, 1991

[54] PROCESSES FOR (3S,4R)-3-[1(R)-T-BUTYL-DIMETHYL-SILYLOXY)-ETHYL]-4-[1-OXO-3-THI-OLANYLTHIO(THIOCARBONYL)THI-O]AZETIDIN-2-ONES AND INTERMEDIATES THEREFOR

[75] Inventors: Frank R. Busch, Gales Ferry; Robert W. Dugger, Mystic; George J. Quallich, North Stonington, all of Conn.

[73] Assignee: Pfizer Inc., New York, N.Y.

[21] Appl. No.: 644,189

[22] Filed: Jan. 18, 1991

Related U.S. Application Data

[62] Division of Ser. No. 569,268, Aug. 17, 1990, abandoned, which is a division of Ser. No. 456,185, Dec. 15, 1989, abandoned, which is a division of Ser. No. 344,159, Apr. 26, 1989, abandoned.

[51] Int. Cl.$^5$ ............... C07D 205/09; C07D 409/12; C07B 37/10; C07F 7/18
[52] U.S. Cl. ............................ 540/359; 540/357
[58] Field of Search ........................... 540/359

[56] References Cited

U.S. PATENT DOCUMENTS

| 4,585,767 | 4/1986 | Cooke et al. | 514/210 |
|---|---|---|---|
| 4,595,539 | 6/1986 | Hamanaka | 260/239 A |
| 4,614,614 | 9/1986 | Ernest et al. | 540/359 |
| 4,619,783 | 10/1986 | Hamanaka | 540/361 |
| 4,619,924 | 10/1986 | Hamanaka | 514/195 |
| 4,739,047 | 4/1988 | Volkmann et al. | 540/310 |
| 4,740,595 | 4/1988 | Chackalamannil | 540/200 |
| 4,882,429 | 11/1989 | McCombie | 540/200 |

FOREIGN PATENT DOCUMENTS

| 181831 | 5/1986 | European Pat. Off. |
| 58-109490 | 6/1983 | Japan |
| 60-61566 | 4/1985 | Japan |
| 63-45251 | 2/1988 | Japan |
| WO88/08845 | 1/1988 | PCT Int'l Appl. |
| 2048261 | 10/1980 | United Kingdom |
| 2144419 | 3/1985 | United Kingdom |

OTHER PUBLICATIONS

Endo, Can. J. Chem., 65, 2140 (1987).
Leanza et al., Tetrahedron, 39, 2505 (1983).
Yoshida et al., Chem. Pharm. Bull. 29, 2899 (1981).
Alpegiani et al., Tetrahedron Lett., 24, 1627 (1983).
Hirai et al., Tetrahedron Lett., 23, 4021, 4025 (1982).
Yanagisawa, Tet. Letters 24, 1037–40.
Shiozaki, Tet. Letters 22, 5205 (1981).
Maruyana, Tet. Letters 26, 4521 (1985).

*Primary Examiner*—Mark L. Berch
*Attorney, Agent, or Firm*—Peter C. Richardson; J. Trevor Lumb; Mervin E. Brokke

[57] ABSTRACT

Improved processes for preparation of racemic, cis- and optically active (3S,4R)-3[1(R)-t-butyl-dimethylsilyloxy)-ethyl]-4-[1-oxo-3-thiolanylthio(thiocarbonyl)thio]azetidin-2-ones, process improvements for certain intermediates therefor and a novel intermediate for said racemic, cis- and trans-compounds, which compounds are useful as intermediates for antibacterial 5R,6S-6-[1(R)-hydroxyethyl]-2-(1-oxo-3-thiolanylthio)-2-penem-3-carboxylic acids and the pharmaceutically-acceptable salts and the pivaloyloxymethyl esters thereof.

2 Claims, No Drawings

PROCESSES FOR (3S,4R)-3-[1(R)-T-BUTYL-DIMETHYLSILYLOXY)-ETHYL]-4-[1-OXO-3-THIOLANYLTHIO(THI-OCARBONYL)THIO]AZETIDIN-2-ONES AND INTERMEDIATES THEREFOR

This is a division of application Ser. No. 07/569,268, filed on Aug. 17, 1990, abandoned, which is a division of application Ser. No. 07/456,185, filed on Dec. 15, 1989, now abandoned; which is a division of Ser. No. 07/344,159, filed on Apr. 26, 1989, now abandoned.

BACKGROUND OF THE INVENTION

1. Field of the Invention

This invention relates to improved processes for making (3S,4R)-3-[1(R)-(t-butyldimethylsilyloxy)ethyl]-4-[1-oxo-3-thiolanylthio(thiocarbonyl)thio]azetidin-2-ones of the formula

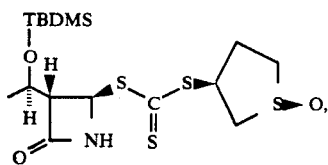

which formula includes the racemic, cis- and optically active forms of the 4-position substituent of formula (I). It also relates to improvements in processes for making certain intermediates for formula (I) compounds and to a novel intermediate for formula (I) compounds.

Compounds of formula (I) are valuable intermediates for antibacterial 5R,6S-6-[1(R)-hydroxyethyl]-2-(1-oxo-3-thiolanylthio)-2-penem-3-carboxylic acids, formula (II), pharmaceutically-acceptable salts thereof and esters, especially the pivaloyloxymethyl esters, thereof:

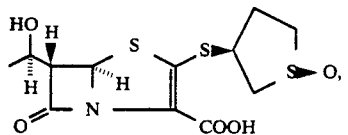

wherein said formula represents racemic, cis- and optically active forms of the 1-oxo-3-thiolanylthio moiety of (II).

2. Description of Related Art

Processes for the synthesis of penem compounds of formula (II) are described in U.S. Pat. Nos. 4,595,539 and 4,619,783. The first patent describes desulfurization of a xanthate or trithiocarbonate such as, for example, a p-nitrobenzyl-2-(4-alkylthio-2-oxo-1-azetidinyl)-2-[2-$R_1$thio(thiocarbonyl)thio]acetate (wherein $R_1$ represents an organic moiety) followed by addition of an electrophilic reactant, e.g. acetyl chloride, to give the corresponding p-nitrobenzyl 2(4-alkylthio-2-oxo-1-azetidinyl)-3-acetylthio-3-(2-$R_1$-thioacrylate. The acrylate derivative is then converted to the corresponding 4-halo derivative by halogenation and then cyclized to give a penem.

The second patent, U.S. Pat. No. 4,619,783, describes the process comprising desulfurization of a xanthate or trithiocarbonate such as a p-nitrobenzyl 2-{4-alkylthio-3-[1-(p-nitrobenzyloxycarbonyloxy)ethyl]-2-oxo-1-azetidinyl}-2-($R_1$oxythiocarbonylthio)acetate to the corresponding 2-($R_1$oxythiocarbonyl)acetate, followed by halogenation to the corresponding 4-halo derivative and cyclization to a 2-penem.

Each of the afore-mentioned patents also discloses conversion of 4-acetoxy-3-R-azetidin-2-ones (wherein R=H, 1-hydroxyalkyl or protected 1-hydroxyalkyl) to the corresponding 4-alkylthio-3-R-azetidin-2-ones by reaction with the sodium salt of the appropriate alkanethiol.

U.S. Pat. No. 4,619,924 describes reaction of 4-acetoxy-3[1(R)-(t-butyldimethylsilyloxy)ethyl]azetidin-2-one with sodium or potassium trithiocarbonates of the formula $Na^+R_1$—S—C(S)—S wherein $R_1$ is an organic moiety to produce the corresponding 4-R-thio(thiocarbonyl)thioazetidin-2-one, e.g., of formula (I), and subsequent conversion of said azetidin-2-one to a compound of formula (II).

Compounds of formula (I) and (II) and their preparation from (3R,4R)-4-acetoxy-3-[1(R)-(t-butyldimethylsilyloxy)ethyl]azetidin-2-one are described in U.S. Pat. No. 4,739,047.

Methods of preparing a number of (3S,4R)-3-[1(R)-hydroxyethyl]-4-(X-substituted)azetidin-2-ones of formula (III)

which may bear a protecting group on the hydroxy group and/or nitrogen atom, and their use as intermediates, are reported in the literature. Representative of such compounds are the following:

| X | Reference |
|---|---|
| Cl | Alpegiani et al., Tetrahedron Lett. 24, 1627 (1983). |
| | Endo, Can. J. Chem. 65, 2140 (1987). |
| S-t-butyl | Endo, Can. J. Chem. 65, 2140 (1987). |
| OCOCH$_3$ | Leanza et al., Tetrahedron 39, 2505 (1983). |
| OCOC$_6$H$_5$ | EP-181831, published May 21, 1986. |
| COOC$_6$H$_5$ | |
| COO(4-NO$_2$C$_6$H$_4$) | U.S. Pat. No. 4,614,614, issued September 30, 1986. |
| SO$_2$(4-NO$_2$C$_6$H$_4$) | |
| SO$_2$[2,4-(NO$_2$)$_2$C$_6$H$_3$] | |
| SO$_2$CH$_3$ | Yoshida et al., Chem. Pharm. Bull. 29, 2899 (1981). |
| SO$_2$C$_6$H$_5$ | Yoshida et al. (loc. cit.). |
| | Hirai et al., Tetrahedron Lett. 23, 4021, 1982. |
| | U.S. Pat. No. 4,614,614, issued September 30, 1986. |
| | Shiozaki et al., Tetrahedron Lett. 22, 5205 (1981). |
| | Shibasaki et al., J. Chem. Soc., Chem. Commun. 1324 (1982). |
| | Yanagisawa et al., Tetrahedron Lett. 24, 1037 (1983). |
| S(C$_{1-8}$alkyl) | U.S. Pat. No. 4,585,767, issued April 29, 1986. |

A multistep synthesis of (3R,4R)-3-[1(R)-(t-butyl-dimethylsiloxy)ethyl]-4-methylsulfonylazetidin-2-one (formula III, X=SO$_2$CH$_3$) from methyl (3S,5R,6S)-6-bromo-6[1(R)-hydroxyethyl]penicillanate is reported by Hirai et al., Tetrahedron Lett. 23, 4021 (1982). The synthesis involves tin hydride debromination of the starting material followed by protection of the hydroxy group of the 6-substituent by silylation with t-butyldimethylsilyl chloride and oxidation of the resulting product to the cis sulfone derivative. The crucial step of the synthesis, reported to be isomerization of the cis sulfone to the trans sulfone, was "satisfactorily" achieved by means of a catalytic amount of 1,5-diazabicyclo [4.3.0]non-5-ene (DBN) in methylene chloride at room temperature. Ring opening of the trans sulfone by treatment with excess methyl iodide and potassium t-butoxide afforded 3-[1(R)-(t-butyldimethylsiloxy)-ethyl]-4-methylsulfonylazetidin-2-one.

However, applicants have found that while DBN does achieve isomerization of the cis sulfone to the trans sulfone, as reported by Hirai et al. (loc. cit.), it fails to completely isomerize the protected hydroxyethyl group. Subsequent opening of the ring of the trans sulfone to afford the corresponding azetidinone in the Hirai et al. process by treating the sulfone with excess methyl iodide and potassium t-butoxide gave a mixture of isomers.

Japanese patent specification No. SHO 58-109490, published June 29, 1983, discloses that conversion of the 5,6-cis-compound of formula (IV)

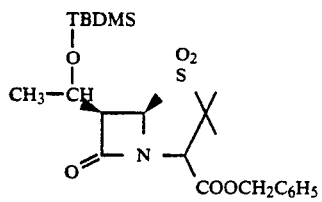

to the corresponding trans compound can be accomplished by treating the cis compound with any of a variety of organic bases such as DBN, DBU (1,8-diazabicyclo[5.4.0]-undec-7-ene, triethylamine and N,N-dimethylaniline. The disclosure notes the amount of base used can be a catalytic amount, but is usually 0.1 to 2 equivalents. However, it exemplifies the use of only DBN as isomerizing agent.

The synthesis of (III) wherein X is $SO_2C_6H_5$ as described by Yanagisawa et al. (loc. cit.) involves, as one step, transformation of the epoxysulfone (V) to azetidin-2-one (III-A) in 82% yield

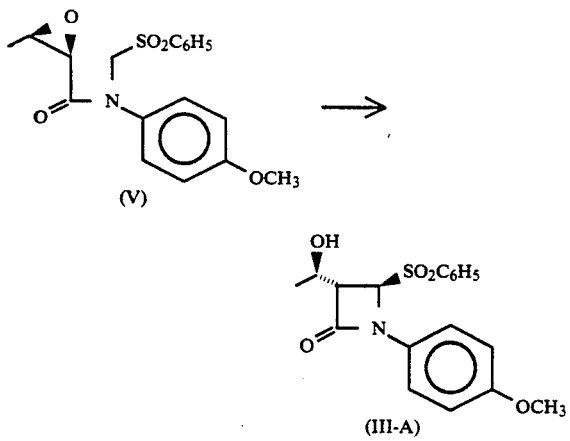

by reaction with n-butyllithium (2-equivalents) in hexamethylphosphoric triamide (HMPT)-tetrahydrofuran at −50° C. in an inert atmosphere. When the reaction was conducted in the absence of HMPT, the temperature had to be increased to room temperature. The product was a 3:1 mixture of (III-A) and its diastereomer.

U.S. Pat. No. 4,614,614 describes a process for converting (V) to (III-A) by treating (V) with a source of fluoride ion, e.g. tetra(n-butyl)ammonium fluoride in an aprotic solvent. Broad disclosure is presented to (3S) 3,4-trans disubstituted azetidin-2-ones wherein the 3-substituent is 1-hydroxyethyl or hydroxymethyl, optionally protected, and the 4-substituent is, inter alia, $-SO_2R_3$ wherein $R_3$ is an organic radical linked to the S atom by a carbon atom not bonded to hydrogen; or the 4-substituent is $COOR_3'$ wherein $R_e'$ is an organic radical linked to the O atom of the carboxy group by a carbon atom not bonded to hydrogen. Representative examples of $R_3$ and $R_3'$ are tert-lower alkyl, aryl, e.g. phenyl, or substituted aryl wherein the substituent is, for example, methoxy, methyl or nitro.

Shibasaki et al. (loc. cit.) report preparation of (III) wherein X is $SO_2C_6H_5$ by oxidation of the corresponding compound wherein X is $SC_6H_5$. A related oxidation procedure is described by Yoshida et al. (loc. cit.).

Shiozaki et al. (loc. cit.) report preparation of (III, $X=SO_2C_6H_5$) by treatment of (III, $X=OCOCH_3$) with two equivalents of sodium phenyl sulfonate in 63% yield.

Preparation of (III, X=Cl) is disclosed by Alpegiani et al. (loc. cit.), the process comprising reaction of appropriate disulfides (III, X=-S-S-2-benzothiazolyl) with one molar equivalent of chlorine. It is described as being unstable to silica gel chromatography. Endo (loc. cit.) teaches its preparation by chlorinolysis of (III, X=t-butylsulfide) with two equivalents of chlorine. He discloses it "is rather unstable at room temperature but reasonably stable at −20° C.," and notes its high reactivity at low temperatures relative to that of the acetoxy derivative (III, $X=OCOCH_3$).

EP-181831 presents a broad disclosure of formula (III) compounds wherein X is $-OCOR_3$ wherein $R_3$ is lower alkyl, phenyl or substituted phenyl. The latter group is, for example, mono- to trisubstituted by groups such as lower alkoxy, lower alkyl and/or halogen.

U.S. Pat. No. 4,585,767 discloses preparation of 6-(1-hydroxyethyl)-2-aryloxy penems from 3-(1-hydroxyethyl)-4-substituted-azetidin-2-ones wherein the 4-substituent is a group capable of replacement by a nucleophilic group and is especially an acyloxy (e.g., acetoxy), sulphonyl (e.g., phenylsulphonyl) or halo (e.g., chloro).

Compounds related to those of formula (III) but in which the 3-position is unsubstituted or is substituted by one or two methyl groups and the 4-substituent is -YZ wherein Y is O, S or $SO_2$ and Z is alkyl, phenyl, substituted phenyl, alkanoyl, benzoyl or substituted benzoyl are known from Clauss et al., Liebigs Ann. chem 539 (1974). The 4-acyloxy derivatives enumerated above serve as reactants for the other 4-substituted derivatives cited by nucleophilic displacement of the acyloxy group.

Procedures for preparing and for recovering (3S,4R)-3-[1(R)-(t-butyldimethylsilyloxy)ethyl]-4-[1-oxo-3-thiolanylthio(thiocarbonyl)thio]azetidin-2-ones (I) from reaction mixtures thereof are described in U.S. Pat. No. 4,739,047, issued Apr. 19, 1988 which exemplifies preparation of (3S,4R)-3-[1(R)-(t-butyldimethylsilyloxy)-ethyl]-4-[1(R)-oxo-3S-thiolanylthio(thiocarbonyl)thio]-azetidin-2-one by reaction of (3R,4R)-4-acetoxy-3-[1(R)-(t-butyldimethylsilyloxy)ethyl]azetidin-2-one with sodium 3S-(thio(thiocarbonyl)thio)thiolane 1(R)-oxide. The product was recovered by quenching the reaction with saturated ammonium chloride solution followed by extraction of the product with ethyl acetate and concentration of the dried extract. The crude product was purified by slurring it in isopropylether.

The above procedure involves aqueous steps which, while satisfactory for small scale reactions, are not suitable for large scale work-up due to poor stability of (I) under aqueous work-up procedures.

SUMMARY OF THE INVENTION

This invention is directed to improvements in processes for making certain intermediates for 5R,6S-6[1(R)-hydroxyethyl]-2-(1-oxo-3-thiolanylthio)-2-penem-3-carboxylic acids and the pharmaceutically acceptable salts and pivaloyloxymethyl esters thereof. More particularly, it relates to improved processes for making racemic, cis- and optically active (3S,4R)-3[1(R)-t-butyldimethylsilyloxy)ethyl]-4-[1-oxo-3-thiolanylthio(thiocarbonyl)thio]azetidin-2-ones, formula (I); to improvements in processes for making certain (3S,4R)-3[1(R)-(t-butyldimethylsilyloxy)ethyl]-4-substituted)azetidin-2-ones wherein the 4-substituent is SO₂Y wherein Y is methyl or 2,4-dinitrophenyl via route (1)

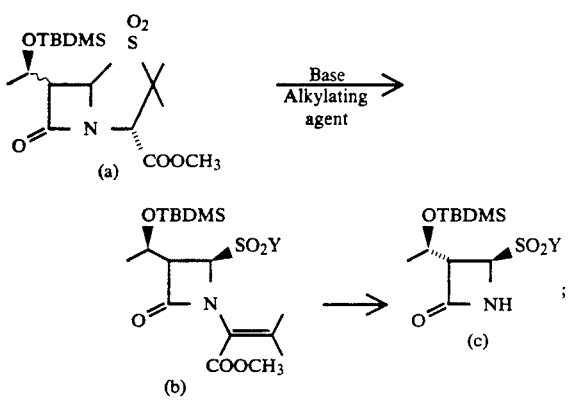

or wherein the 4-substituent is SO₂C₆H₅ via route (2)

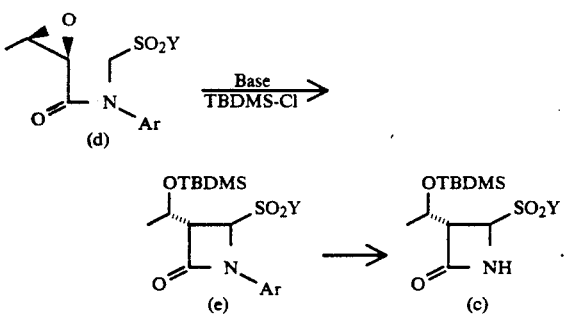

wherein Ar is an amino protecting group.

Still further, it relates to a novel intermediate (VI)

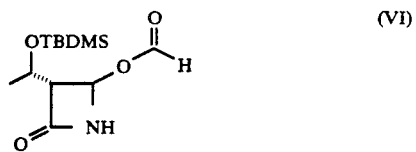

for preparation of (I); and to an improved, non-aqueous process for recovering (I) from reaction mixtures thereof.

DETAILED DESCRIPTION OF THE INVENTION

The process of route (1) above reported by Hirai et al. (loc. cit.) uses DBN as base for isomerization of the cis form of (a) to the trans form. They report use of a catalytic amount of DBN in methylene chloride at room temperature afforded satisfactory conversion. However, applicants have found that DBN fails to completely isomerize cis (a) to trans (a) with the result that upon ring opening of the isomerization reaction product, a mixture of the cis and trans forms of (b) is obtained.

However, DBU has been found to achieve complete isomerization of cis (a) to trans (a). Subsequent ring opening of the isomerization product then affords only the trans form of (b), eliminating the need to separate isomers at this point or at a later point in a reaction scheme wherein (b) may be used as intermediate.

The reaction with DBU is carried out in substantially the same manner as is that with DBN. The amount of DBU, based upon reactant (a), used can vary from a catalytic amount (less than 0.1 mole equivalent) to a large excess of DBU. In order to achieve complete isomerization of the cis to the trans form, greater than one mole equivalent of DBU must be used. An amount of DBU ranging form about 1.0 to 2.0 mole equivalents has been found particularly valuable in bringing about complete isomerization of cis (a) to trans (a). Methylene chloride serves well as reaction-inert solvent. Reaction periods of about 5-90 minutes at ambient temperature afford substantially complete isomerization of cis to trans isomer. Addition of an alkylating or arylating agent, e.g. methyl iodide, 2,4-dinitrofluorobenzene or 2,4-dinitrochlorobenzene, to the isomerization reaction product produces the formula (b) compound after beta-elimination of the thiazolidine ring. In practice, the step of alkylation or arylation is conducted by adding the alkylating or arylating agent to the isomerization reaction product after subsequent beta-elimination of the thiazolidine ring, a 1 to 4 fold excess of said agent being used. The reaction is a one-pot process; i.e., it is carried out in a single reactor without isolation of intermediates. The temperature of the reaction is from about 0° C. to 10° C. when using methyl iodide as aklylating agent, and from about 20° C. to 50° C. when using an arylating agent. The products are recovered by known procedures.

Conversion of formula (b) to formula (c) compounds is carried out by oxidation procedures reported in the literature.

The route (2) process for conversion of glycidic amide (d) to azetidinone (e) is carried out by treating the glycidic amide in a reaction-inert solvent such as tetrahydrofuran with lithium t-butoxide, a weaker base than that used by Yanagisawa et al. (loc. cit.). The use of lithium t-butoxide affords advantages of economy and ease of handling over the use of n-butyllithium. Its successful use is surprising and unexpected in view of the failure of potassium t-butoxide to bring about the conversion.

The novel formyloxy derivative of formula (VI) is prepared by reacting the corresponding chloro derivative with formic acid in the presence of a base. An excess of formic acid is used, e.g., from 2-5 fold excess, together with sufficient base to neutralize the formic acid. While any base can be used, an organic base such as triethylamine, dimethylaniline, pyridine and N-methylmorpholine are favored. The reaction is carried out at about 0°–10° C. and the product recovered by known procedures.

It serves as a valuable intermediate for preparation of formula (I) compounds and is superior in reaction rate and yield to (3S,4R)-3-[1(R)-(t-butyldimethylsilyloxy)ethyl]-4-acetoxyazetidin-2-one.

Formula (I) products are prepared by reacting a 3R,4R-4-substituted-3-[1(R)-1-(dimethyl-t-butylsilyloxy)ethyl]azetidin-2-one with racemic cis or optically active form of 3-[thio(thiocarbonyl)thio]thiolane-1-oxide in a reaction-inert solvent. By reaction-inert solvent is meant a solvent which does not react with reactants or products in such a way as to substantially reduce the yield of the desired product. Appropriate 4-substituted azetidin-2-one reactants are those wherein the 4-substituent is chloro, acetoxy, formyloxy or 2,4-dinitrophenylsulfonyl. Representative reaction-inert solvents are isopropyl alcohol and aprotic solvents such as those enumerated below. It has been found that the particular conditions for this reaction are influenced, in part, by the 4-substituent of the azetidin-2-one reactant. In general, favored reaction-inert solvents are aprotic solvents (e.g., acetone, methylene chloride, chloroform, tetrahydrofuran, ethyl acetate and mixtures thereof). The preferred aprotic solvent is acetone. The reaction is conducted at from about $-10°$ C. to $+10°$ C. for periods of from about 15 minutes to two hours. Although the stoichiometry of the reaction calls for equimolar amounts of reactants, an excess, from about 3–10% molar excess, of the appropriate 3-[thio(thiocarbonyl)thio]thiolane-1-oxide as its alkali metal, preferably sodium, salt has been found to be advantageous in actual practice.

The formula (I) products are recovered in improved yields and in high quality from reactions containing them by non-aqueous work-up conditions. The general procedure comprises quenching the reaction with an aprotic solvent or mixture of aprotic solvents and recovering the product which separates out by filtration or centrifugation.

Surprisingly, in view of the poor stability of (I) under aqueous work-up procedures as noted above, it has been found that when the azetidin-2-one reactant in the above-mentioned process is 3R,4R-4-acetoxy-3-[1(R)-1-(dimethyl-t-butylsilyloxy)ethyl]azetidin-2-one and the reaction-inert solvent is isopropyl alcohol, a methylene chloride/saturated aqueous ammonium chloride quench followed by concentration of the quench mixture and addition of isopropyl ether to the concentrate affords good quality product.

EXAMPLE 1

(3R,4R)-4-Methylsulphonyl-3[1(R)-(t-butyldimethylsilyloxy)ethyl]-1-(1-methoxycarbonyl-2-methyl-1-propenyl)azetidin-2-one To a solution containing the isomers methyl-(3S,5R,6S)-6-[1(R)-(t-butyldimethylsilyloxy)ethyl)-penicillanate S,S-dioxide and methyl(3S,5R,6R)-6-[1(R)-(t-butyldimethylsilyloxy)ethyl]penicillanate S,S-dioxide (34.9 g, 0.086 mole) in methylene chloride (200 ml) at ambient temperature was added 1,8-diazabicyclo [5.4.0]undec-7-ene (DBU 17.02 g, 112 mole) dropwise over a 5 minute period. The reaction was then stirred for 90 minutes, cooled to 0° C. and methyl iodide (53.5 g, 0.375 mole) added over 10 minutes. Stirring was continued at 0° C. for 16 hours. The reaction was diluted with methylene chloride (200 ml) and washed with pH 3 water (2×400 ml), water (250 ml), and saturated NaHCO$_3$ (250 ml). Treatment of the organic extract with Na$_2$SO$_4$ and removal of the solvent produced a viscous oil, 33.6 g, 93%. IR(CHCl$_3$) 2953, 2930, 2887, 2857, 1778, 1715, 1624, 1437, 1383, 1321, 1144 cm$^{-1}$.

NMR(250 MHz) 5.29 (d, J=2.4 Hz, 1H), 4.34 (dq, 1H), 3.79 (s, 3H), 3.61 (dd, J=2.4 Hz, J=3.1 Hz, 1H), 2.86 (s, 3H), 2.24 (s, 3H), 2.06 (s, 3H), 1.30 (d, J=6 Hz, 3H), 0.86 (s, 9H), 0.10 (s, 3H), 0.06 (s, 3H).

Analysis calculated for C$_{18}$H$_{33}$NO$_6$SSi:
C, 51.52; H, 7.93; N, 3.34; S, 7.64%.
Found: C, 50.52; H, 7.47; N, 3.14; S, 7.46%.

EXAMPLE 2

(3R,4R)-3[1(R)-(t-butyldimethylsilyloxy)-ethyl]-4-methylsulphonylazetidin-2-one

Phosphate buffer (pH 7, 680 ml), potassium permanganate (0.98 g, 0.006 mole), sodium periodate (87.3 g, 0.41 mole) and acetone (320 ml) were combined at ambient temperature and then cooled to 0° C. Over 8 minutes unsaturated ester of Example 1 (33.6 g, 0.08 mole) in acetone (320 ml) was added. The reaction was stirred 30 minutes at 0°–5° C. and then allowed to warm to ambient temperature. Over 1 hour reaction time the purple solution had changed to a pink color, and 30 ml of aqueous potassium permanganate (15 g, 0.095 mole in 500 ml water) was added. At 1 hour intervals, two more portions (50 ml and 75 ml) of aqueous potassium permanganate were added. The reaction was complete after 6 hours. Water (500 ml) and ethyl acetate were added, and the phases separated. The aqueous phase was extracted with ethyl acetate (3×250 ml). The combined organic layers were washed with water (2×500 ml), dried with sodium sulfate, and solvent removed under vacuum yielding 22.7 g (92%) of a thick colorless oil. Crystals formed on standing at 0° C.; m.p. 101°–102° C. IR(CHCl$_3$) 3404, 2950, 2930, 2886, 2856, 1793, 1463, 1321, 1145, 1128 cm$^{-1}$. NMR(250 MHz) 6.53 (bs, 1H), 4.74 (d, J=2.1 Hz, 1H), 4.32 (m, 1H), 3.56 (t, J=2.5 Hz, 1H), 2.96 (s, 3H), 1.26 (d, J=6 Hz, 3H), 0.86 (s, 9H), 0.07 (s, 3H), 0.05 (s, 3H).

Analysis calculated for C$_{12}$H$_{25}$NO$_4$SSi:
C, 46.87; H, 8.20; N, 4.56; S, 10.43%.

Found: C, 46.83; H, 8.15; N, 4,33; S, 10.36%.

EXAMPLE 3

(3R,4R)-4-(2,4-Dinitrophenylsulphonyl)-3-[1(R)-(t-butyldimethylsilyloxy)ethyl]-1-(1-methoxycarbonyl-2-methyl-1-propenyl)azetidin-2-one The procedure of Example 1 was followed but using 25 g (61.7 mmole) of the isomeric mixture of methyl 6-[1-(R)-(t-butyldimethylsiloxy)ethyl]penicillanate S,S-dioxides, 12 ml (80.6 mmole) of DBU, 12.5 g (61.7 mmole) of 2,4-dinitrochlorobenzene and 138 ml of methylene chloride to provide 64% yield of the title compound after chromatography with 20% ethyl acetate/hexene on silica. MS m/e 514 (56), 340 (26), 288 (32), 281 (23), 207 (19), 182 (15) 158 (42), 73 (100). IR(CHCl$_3$) 2933, 2858, 1788, 1726, 1609, 1545, 1464, 1437, 1352, 1305, 1247, 1154, 1129, 1100, 1061 cm$^{-1}$. NMR (250 MHz) 8.65 (d, J=2.5 Hz, 1H), 8.50 (dd, J=2.5 Hz, J=8 Hz, 1H), 8.12 (d, J=8 Hz, 1H), 6.18 (d, J=3 Hz, 1H), 4.39 (bq, J=3 Hz, 1H), 3.88 (t, J=3 Hz, 1H), 3.47 (s, 3H), 2.08 (s, 3H), 2.06 (s, 3H), 1.30 (d, J=7 Hz, 3H), 0.82 (s, 9H), 0.10 (s, 3H), 0.02 (s, 3H).

EXAMPLE 4

(3R,4R)-3[1(R)-(t-butyldimethylsilyloxy)ethyl]-4-(2,4-dinitrophenylsulphonyl)azetidin-2-one The unsaturated ester (20.25 g, 35.6 mmole) of Example 3 was combined with carbon tetrachloride (81 ml), acetonitrile (81 ml), sodium periodate (15.22 g, 71.6 mmoles) and water (122 ml) at ambient temperature. To this biphasic solution was added a solution of ruthenium trichloride trihydrate in acetonitrile (23.1 ml) made from 500 mg of ruthenium trichloride trihydrate in 25 ml of acetonitrile. After stirring for 4 hours, methylene chloride (200 ml) and a saturated aqueous solution of sodium bicarbonate (200 ml) were added and the phases separated. The aqueous phase was again extracted with methylene chloride (3×200 ml), the organic extracts combined, dried with magnesium sulfate and solvents removed under vacuum. The oxamate product was obtained as a white solid (17.79 g, 92%).

This oxidative cleavage was also achieved with ozone as follows. A solution of unsaturated ester (0.2 g) in methylene chloride (5 ml) was cooled to 78° C. Ozone was bubbled into the solution until thin layer chromatography showed that all the starting material was consumed. Nitrogen was bubbled through the solution to remove excess ozone, and then dimethyl sulfide (1 ml) was added allowing the flask to warm to ambient temperature with stirring for 1 hour. The organic phase was washed with water (20 ml), aqueous saturated sodium bicarbonate (20 ml) and water (2×15 ml). After drying the organic phase with sodium sulfate and removal of the solvent, 198 mg of the oxamate product was obtained as a white solid. NMR (250 MHz) 8.75 (d, J=2.5 Hz, 1H), 8.60 (dd, J=2.5 Hz, J=8 Hz, 1H), 8.35 (d, J=8 Hz, 1H), 6.29 (d, J=3 Hz, 1H), 4.54 (dq, J=7 Hz, J=2 Hz, 1H), 4.09 (t, J=2 Hz, 1H), 3.91 (s, 3H), 1.40 (d, J=7 Hz, 3H), 0.82 (s, 9H), 0.13 (s, 3H), 0.04 (s, 3H).

To a solution of oxamate (17.79 g) in tetrahydrofuran 360 ml) was added pH 7 buffer (180 ml) at ambient temperature. This solution was stirred 18 hours at ambient temperature. The solvent was removed under vacuum and ethyl acetate (250 ml) and saturated aqueous sodium bicarbonate (250 ml) was added. The phases were separated and the aqueous phase extracted with ethyl acetate (3×250 ml). The combined organic extracts were dried with magnesium sulfate and the solvent removed under vacuum to yield 12.1 g of crude title product. This material was purified by granulating with chloroform (15 ml) for 30 minutes. The product was filtered off as a white solid (9.936 g, 67%). A second crop of product was obtained from the filtrate, chloroform/hexane, (450 mg) affording a total yield of 70%; m.p. 148°-149° C. NMR(250 MHz) 8.6-8.7 (m, 2H), 8.44 (d, J=8 Hz, 1H), 6.55 (bs, 1H), 4.36 (dq, J=3 Hz, J=7 Hz, 1H), 3.85 (t, J=3 Hz, 1H), 1.24 (d, J=7 Hz, 3H), 0.83 (s, 9H), 0.09 (s, 3H), 0.03 (s, 3H).

EXAMPLE 5

(3R,4R)-4-Formyloxy-3[1(R)-(t-butyldimethylsilyloxy)ethyl]azetidin-2-one

Triethylamine (21.12 ml) was added dropwise, with stirring, to a solution of formic acid (5.72 ml) in methylene chloride (80 ml) over a ten minute period at 10°-12° C. The reaction was then cooled to 0° C. and (3R,4R)-4-chloro-3[1(R)-t-butyldimethylsilyloxy)ethyl]-azetidin-2-one (8.0 g) in methylene chloride (80 ml) added dropwise at such a rate that the temperature did not rise above 1° C.

The reaction was stirred for one hour at 0° C. following completion of addition, then quenched by pouring into pH 7.0 buffer (80 ml). The methylene chloride layer was separated, washed with pH 7.0 buffer (4×80 ml), then dried (Aa₂SO₄) and stripped under reduced pressure to give 5.4 g of crude title product. The crude was chromatographed on 150 g of silica (70-230 mesh) using ethyl acetate/hexane (20:80) as solvent system. Fractions of 800 drop volume were collected. Fractions 31-75 were combined and stripped to afford 2.6 g of white solid. Said solid was rechromatographed under the same conditions to give 2.1 g (31%) of white crystalline product; m.p. 75°-76° C.

EXAMPLE 6

3S,4R-3-[1(R)-(Dimethyl-t-butylsilyloxy)ethyl]-4-[cis-1-oxo-3S-thiolanylthio-(thiocarbonyl)thio]-2-azetidinone A 250 ml three necked flask, purged with dry nitrogen, and equipped with a mechanical stirrer, thermometer, and addition funnel was charged with cis-3S-(acetylthio)thiolane 1-oxide (11.4 g, 64.0 mmole) and 120 ml of isopropyl alcohol. This was cooled to −10° C. and sodium methoxide (3.71 g, 69 mmole) was added over 2 minutes. After stirring at 0° C. for about 30 minutes 17.5 ml of carbon disulfide was added. A slurry formed which was stirred for 1 hour. The reaction was separated into two equal portions (one for processing and the other for a stability study). A solution of 10.05 g (35 mmole) of 3R,4R-4-acetoxy-3-[1(R)-1-dimethyl-t-butylsilyloxy)ethyl]-2-azetidinone in 50 ml of methylene chloride was added dropwise to the reaction at −15° to −5° C. over 22 minutes. Then the reaction was stirred and monitored by TLC (silica gel 9:1 ethyl acetate/methanol). The reaction was judged to be complete after 30 minutes. The reaction was concentrated at −5° to 5° C. at reduced pressure. The resulting oil was taken up in about 50 ml of methylene chloride and the inorganic solids were filtered. The filtrate was again concentrated at reduced pressure, then the product was precipitated from methylene chloride/isopropyl ether. The product was dried in the vacuum oven without heat overnight. Yield=41%.

EXAMPLE 7

(3S,4R)-3-[1(R)-(t-butyldimethylsilyl oxy)ethyl]-4-[1(R)-oxo-3S-thiolanylthio(thiocarbonyl)-thio]azetidin-2-one The procedure of Example 6 is followed except that 5.69 g of 3R,4R-4-formyloxy-3-[1(R)-1-(t-butyldimethylsilyloxy)ethyl]azetidin-2-one is used in place of the 4-acetoxy azetidin-2-one of said example. The title product is recovered as a solid.

In like manner the same product is prepared using the following 4-substituted azetidin-2-one as reactant:

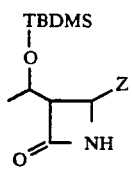

Z = SO₂[2,4-(NO₂)₂C₆H₃]
TBDMS = t-butyldimethylsilyl

EXAMPLE 8

(3S,4R)-3-[1(R)-(t-butyldimethylsilyloxy)ethyl]-4-[1(R)-oxo-3S-thiolanylthio-(thiocarbonyl)thio]azetidin-2-one A three-neck flask was fitted with a thermometer, magnetic stirrer and dropping funnel. It was purged with dry nitrogen and charged with 3R,4R-4-chloro-3[1(R)-1-(t-butyldimethylsilyloxy)ethyl]azetidin-2-one (3.8 g of 80% material; equivalent to 3.11 g of pure material) dissolved in acetone (35 ml). The solution was cooled to −2° C. and sodium 3S-[thio(thiocarbonyl)-thio]thiolane 1R-oxide (3.409 of 80% material, equivalent to 2.7 g of pure material) added in one portion. The reaction was stirred for 70 minutes at −2° C. at which time methylene chloride (10 ml) was added and stirring continued for five minutes. The salts which precipitated were filtered off and washed with methylene chloride (5 ml). The filtrate and wash were combined and concentrated under reduced pressure, the resulting solids gave an estimated 88% yield of crude product. The solids were dissolved in methylene chloride (50 ml), the solution treated with sodium sulfate (1 g) and activated carbon (0.4 g) for ten minutes. The solution was then filtered and concentrated under reduced pressure to about 15 ml volume. Isopropyl ether (60 ml) was added dropwise to the concentrate to give a thick slurry. Filtration afforded 3.53 g, 68% yield, of the title product. An additional one gram of product may be recovered from the mother liquors.

EXAMPLE 9

1-N-(p-Methoxyphenyl)-(3S,4R)-3-[1(R)-hydroxyethyl]-4-phenylsulfonylazetidin-2-one To a slurry of N-(p-methoxyphenyl)-N-phenylsulfonylmethyl-(R)-glyceridic acid amide (3 g, 8.3 mM) in tetrahydrofuran (50 ml) at 0° C. was added N,N,N',N'-tetramethylethylenediamine (3.8 ml, 25 mM) and lithium t-butoxide (2 g, 25 mM). The reaction was stirred for three hours at 0° C., then diluted by addition of ethyl acetate (250 ml). It was then washed with 5% hydrochloric acid (3×100 ml), water (1×100 ml) and brine (1×100 ml). The organic solvent mixture was then dried (Na₂SO₄) and stripped under reduced pressure to give 2.9 g of semi-crystalline product. Recrystallization from methanol gave 1.65 g of title product as white crystals; m.p. 191°–195° C. Yield=55%.

EXAMPLE 10

(3S,4R)-3[1(R)-(t-Butyldimethylsilyoxy)-ethyl]-4-[1-oxo-3-thiolanylthio-(thiocarbonyl)thio]azetidin-2-one A 50-gallon glass tank was charged with 1435 g (8.05 moles) of sodium 3S-acetylthiothiolane 1R-oxide and 4.13 gallons of isopropyl alcohol (IPO) and cooled to −5° to 0° C. At that temperature 473 g (8.67 moles) of sodium methylate was added and the reaction stirred for 35 minutes. The reaction was cooled to −10° C. and 2.2 liters (37.5 moles) of carbon disulfide was added. The reaction was stirred for 1 hour. A solution of (3S,4R)-4-acetoxy-3-[1(R)-(t-butyldimethylsilyloxy)-ethyl]azetidin-2-one (2.56 Kg, 1.1 equiv.) was prepared in 4.2 gallons of methylene chloride, then added to the reaction solution over 25 minutes. The reaction was stirred for 28 minutes (reaction is monitored by TLC every 5 minutes, and is quenched as soon as it is done) then quenched by pouring it into a tank containing 21 gallons of methylene chloride and 10.5 gallons of saturated ammonium chloride solution. After separation the organic/product layer was washed with: 12.2 gallons of 20% aqueous calcium chloride (6.38 kg), 8.4 gallons of 50% brine, and with 8.3 gallons of brine. The organic layer was carboned (319 g of Darco), dried over 3.2 Kg of magnesium sulfate, then concentrated in vacuo to about 5 gallons. To this was slowly charged 33.7 gallons of isopropyl ether. The resulting solids were stirred at −5° to 0° C. for an hour, then filtered. The solids were vacuum-dried at 25° C. giving 2.21 kg, 62.5% yield of (3S,4R)-3[1(R)-(t-butyldimethylsilyloxy)-ethyl]-4-[1-oxo-3-thiolanylthio(thiocarbonyl)thio]-azetidin-2-one which was characterized by rotation, high field NMR and HLPC assay and found to be identical with an authentic sample thereof.

I claim:

1. In the process for making (e)

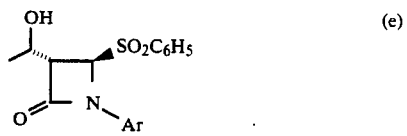

wherein Ar is an amino protecting group by cyclization of (d)

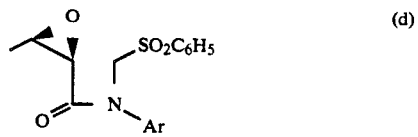

in the presence of a base, the improvement which comprises cyclizing (d) with lithium t-butoxide in a reaction-inert solvent.

2. The process according to claim 1 wherein the molar ratio of lithium t-butoxide to (d) is from about 1.1:1 to 2:1, and Ar is 4-methoxyphenyl or 3,4-dimethoxyphenyl.

* * * * *